(12) United States Patent
Choi et al.

(10) Patent No.: US 6,780,607 B2
(45) Date of Patent: Aug. 24, 2004

(54) METHOD FOR CELL-FREE PROTEIN COMPLETE POST-TRANSLATIONAL MODIFICATION

(75) Inventors: Cha Yong Choi, Seoul (KR); Sang Hyeon Kang, Seoul (KR); Taek Jin Kang, Seoul (KR); Ji Hyoung Woo, Incheon (KR); Sang Kil Lee, Seoul (KR); Seung Woo Cho, Seoul (KR)

(73) Assignee: DreamBiogen Co., Ltd., Seoul (KR)

( * ) Notice: Subject to any disclaimer, the term of this patent is extended or adjusted under 35 U.S.C. 154(b) by 38 days.

(21) Appl. No.: 09/792,647

(22) Filed: Feb. 23, 2001

(65) Prior Publication Data

US 2002/0106719 A1 Aug. 8, 2002

(30) Foreign Application Priority Data

Feb. 7, 2001 (KR) .................................. 2001-0005949

(51) Int. Cl.$^7$ .......................... C12P 21/06; C12P 21/04; C12N 15/00; C12N 5/00; C12N 5/06
(52) U.S. Cl. ....................... 435/68.1; 435/41; 435/69.1; 435/70.1; 435/91.1; 435/175; 435/320.1; 435/325; 435/358; 435/360; 536/23.2
(58) Field of Search ....................... 435/41, 68.1, 69.1, 435/70.1, 91.1, 175, 320.1, 325, 358, 360

(56) References Cited

U.S. PATENT DOCUMENTS

| | | | |
|---|---|---|---|
| 5,324,637 A | | 6/1994 | Thompson et al. ......... 435/68.1 |
| 5,441,868 A | * | 8/1995 | Lin et al. .................... 435/69.4 |
| 6,103,489 A | | 8/2000 | Arakaki et al. ............ 435/68.1 |

OTHER PUBLICATIONS

Seal et al. Neuropharmacol., 1994, vol. 33(9):1065–1070.*
Noren, C.J., et al., "A General Method for Site–Specific Incorporation of Unnatural Amino Acids into Proteins," *Science*, 244, pp. 182–188, 1989.
Prioli, R.P., et al., "Monoclonal Antibodies Against *Trypanosoma cruzi* Neuraminidase Reveal Enzyme Polymorphism, Recognize a Subset of Trypomastigotes, and Enhance Infection in Vitro," *The Journal of Immunology*, 144 (11), pp. 4384–4391, 1990.
Scudder, P., et al., "Characterisation of Oligosaccharides Released from Human–Blood–Group O Erythrocyte Glycopeptides by the Endo–β–Galactosidase of *Bacteroides fragilis*," *European Journal of Biochemistry*, 168, pp. 585–593, 1987.
Tarui, H., et al., "A Novel Cell–free Translation/Glycosylation System Prepared from Insect Cells," *Journal of Bioscience and Bioengineering*, 90 (5), pp. 508–514, 2000.
Boissel, J.P., et al., "Erythropoietin Structure–Function Relationships," *The Journal of Biological Chemistry*, 268 (21), pp. 15983–15993, 1993.
Cavallesco, R., et al., "Antibody to *Trypanosoma cruzi* Neuraminidase Enhances Infection in Vitro and Identifies a Subpopulation of Trypomastigotes," *The Journal of Immunology*, 140 (2), pp. 617–625, 1988.
Dunn, C.D.R., et al., "Technical Components on the Bioassay of Erythropoietin," *Experimental Hemotology*, 6, pp. 577–584, 1978.
Goldwasser, E., et al., "Erythropoietin: Assay and Study of Its Mode of Action," *Methods in Enzymol.*, 37, pp. 109–121, 1975.
Kigawa, T., et al., "Cell–Free Production and Stable–Isotope Labeling of Milligram Quantities of Proteins," *Federation of European Biochemical Societies, Letters* 442, pp. 15–19, 1999.
Kim, D.M., et al., "A Highly Efficient Cell–Free Protein Synthesis System from *Escherichia coli*," *European Journal of Biochemistry*, 239, pp. 881–886, 1996.
Kitamura, T., et al., "Identification and Analysis of Human Erythropoietin Receptors on a Factor–Dependent Cell Line, TF–1," *Blood*, 73 (2), pp. 375–380, 1989.

* cited by examiner

*Primary Examiner*—Manjunath Rao
(74) *Attorney, Agent, or Firm*—Ladas & Parry (57) ABSTRACT

The present invention relates to methods of production of the completely post-translationally modified protein by combination of cell-free protein synthesis and cell-free co- and post-translational modification. Previous cell-free protein synthesis system has only been capable of producing partially post-translationally modified protein but the present invention employs a co- and post-translational modification machinery that produces completely post-translationally modified protein.

9 Claims, 3 Drawing Sheets

Molecular Weight

METHOD FOR CELL-FREE PROTEIN COMPLETE POST-TRANSLATIONAL MODIFICATION

FIELD OF INVENTION

The present invention relates to methods of production of the completely post-translationally modified protein by combination of cell-free protein synthesis and cell-free complete post-translational modification.

BACKGROUND

The present invention relates to protein production of therapeutic, research and commercial value requiring post-translational modification not by a cell culture method but a cell-free completely post-translationally modified protein synthesis method. To explain in more detail, using a cell-free completely post-translationally modified protein synthesis method comprised of cell extract including protein synthesis machinery and cell membrane extract including complete post-translational modification machinery, a valuable protein is produced.

Many pharmacological proteins undergo post-translational modifications such as glycosylation, phosphorylation and amidation etc. that are indispensable for their activity. Moreover, the majority of proteins secreted by mammalian cells are post-translationally modified. Many proteins become post-translationally modified during the 'secretory process', which comprises of a journey from their site of synthesis in the rough endoplasmic reticulum (ER), through the Golgi apparatus and then to various cellular or extracellular destinations. In post-translational modification of a protein, inorganic phosphate is attached to proteins through phosphorylation, amide group is generated at the terminus of polypeptides by amidation and carbohydrate is attached to proteins through glycosylation. Of these, the most complex procedure involving several enzymes is glycosylation. Hence, glycoproteins are the most diverse group of biological compounds that are ubiquitous constituents of almost all living organisms. They occur in cells in both soluble and membrane-bound forms as well as in the extracellular matrix and in intercellular fluids, and they serve a variety of functions. These proteins possess oligosaccharides covalently attached through an asparagine (Asn) side chain ("asparagine-linked" or "N-linked") or through a threonine or serine side chain ("O-linked"). A given glycoprotein may contain N-linked oligosaccharide chains only, O-linked oligosaccharide chains only, or both. The carbohydrate units of glycoproteins exhibit considerable variation in size and structure ranging from mono- or disaccharide to a branched oligosaccharide composed of as many as 20 monosaccharide residues.

In summary, N-linked glycosylation begins with the synthesis of a lipid-linked oligosaccharide moiety, and its transfer en bloc to a nascent polypeptide chain in the ER. Attachment occurs through Asn, generally at the tripeptide recognition sequence Asn-X-Ser/The, where X can be any amino acid from naturally occurring amino acids. A series of trimming reaction is catalyzed by exoglycosidase in the ER. Further processing of N-linked oligosaccharides by mammalian cells continues in the compartment of the Golgi, where a sequence of exoglycosidase- and glycosyltransferase-catalyzed reactions generate high-mannose, hybrid-type and complex-type oligosaccharide structures.

For the biosynthesis of post-translationally modified proteins with biological activity, it is necessary to culture eukaryotic cells capable of undergoing the post-translational modification including glycosylation. The production of post-translationally modified proteins by the culture of such cells, however, costs a great deal, e.g., in right of culture medium cost, operation cost, apparatus cost, etc. This process is also very time-consuming and in order to simplify the process and to save time, many cell-free protein synthesis systems have been developed.

A cell-free protein synthesis has been used as an experimental tool for the investigation of gene expression in vitro especially for the proteins that cannot be synthesized in vivo because of their toxicity to host cells. In addition, various synthetic amino acids besides the 20 natural amino acids can be effectively introduced by this method into protein structures for specially designed purposes (Noren, C. J. et al., Science 244:182–188 (1989)). Moreover, the cell-free protein synthesis has been recently re-evaluated as an alternative to the production of commercially important recombinant proteins, which is mainly due to the recent development of a novel reactor system and the extensive optimization of reactor operating conditions (Kim, D. M. et al., Eur. J. Biochem. 239:881–886 (1996); Kigawa, T. et al., FEBS Lett. 442:15–19 (1999)). Therefore, the development of cell-free protein synthesis systems has reached the next stage, i.e., the production of active proteins on a commercial scale.

Accordingly, some methods were developed to produce the co-translationally modified and the initial post-translationally modified proteins by adding organelles relevant to the co-translational and the initial post-translational modification to these cell-free protein synthesis systems. As a representative method, U.S. Pat. No. 6,103,489 discloses that cell-free assay systems for proteins with the co-translational and the initial post-translational modification have been constructed by combining a eukaryotic cell-free translation system with rough microsome. In another method, the extract including translational components and post-translational modification components such as ER was prepared by a single step extraction from a single source (Hiroshi, T., et al., J. Biosci. Bioeng. 5:508–514 (2000)). In cells, the biosynthesis of many proteins requires co-translational translocation across membranes of an organelle called ER for proper processing. In cell-free systems, in place of the ER, microsomal membranes are used, which are equivalent to the ER in that they contain a high percentage of ER membrane which have been isolated by centrifugation. These reconstituted assay systems for assessing protein translation and the initial post-translational processing in higher eukaryotes have allowed characterization of the translocational machinery, and are being actively used to define the topology of membrane proteins and to elucidate the regulation of N-linked core glycosylation. However, they do not produce the completely post-translationally modified proteins. Since proteins not completely post-translationally modified do not have the complete and correct structure, they cannot be used to study the utility and characteristics of proteins including pharmacological activities. This is due to the fact that proteins with incomplete post-translational modification or no post-translational modification do not or have low biological activity and therefore cannot be used therapeutically. Current cell-free protein synthesis methods cannot produce proteins with a complete structure and therefore is insufficient to be used to study post-translational modifications or functions of genes.

In the meantime, from the results of the Human Genome Project, a great deal of information on the genetics of human have been obtained. In the near future, the complete genome map of humans being will be available. At present, we have reached the Post Genomic Era where the functions of genes and their encoded proteins are being studied. In order to achieve this goal, computer programs that can use information about the sequence of a gene to predict the structure of the encoded protein are used in bioinformatics. From the predicted structure of the protein and the sequence of the gene, the function of the protein can be elucidated. This process of obtaining the function of the protein through prediction is not a completely satisfactory method. A better method would be to express the protein and to study the function through experiments. The protein to be studied should have the complete co- and post-translational modifications. To produce these proteins, the genes of interest should be expressed in a eukaryotic host cell. This process is very time-consuming and in order to simplify the process and to save time, cell-free protein synthesis can be used. Up until now, a cell-free protein synthesis system with a complete post-translational modification has not been developed. Therefore, a cell-free protein synthesis system capable of producing a protein that has undergone complete post-translational modifications needs to be developed.

To solve the problem of prior art that cell-free protein synthesis systems produced incompletely post-translationally modified protein, the present invention provides methods of producing the completely post-translationally modified proteins by a more advanced cell-free protein synthesis system, in particular, by the combination of cell-free protein synthesis and cell-free complete post-translational modification.

We expect that the methods of cell-free protein synthesis according to the present invention can become a useful tool for synthesizing completely post-translationally modified protein for the functional analysis of proteins and the large-scale production of therapeutically important proteins, and to serve as a model system for elucidating the role of proteins and the mechanisms of post-translational modification.

SUMMARY OF THE INVENTION

In order to achieve such goal, the present invention provides a method for preparing completely post-translationally modified protein via coupled cell-free completely post-translationally modified protein synthesis comprising;

adding a DNA template to a cell extract,
adding ribonucleotide triphosphates to the extract, and
adding a sufficient amount of co- and post-translational modification machinery such as ER/Golgi apparatus, or ER/Golgi apparatus/plasma membrane, or other organelles in addition to these to the extract to stimulate the production of completely post-translationally modified protein, or via uncoupled cell-free completely post-translationally modified protein synthesis comprising;

adding a RNA template to a cell extract, and
adding a sufficient amount of co- and post-translational modification machinery such as ER/Golgi apparatus, or ER/Golgi apparatus/plasma membrane, or other organelles in addition to these to the extract to stimulate the production of completely post-translationally modified protein.

The most complex post-translational modification process requiring several enzymes is glycosylation. Correct glycosylation implies that most post-translational modification is possible using the same method.

Reviewing the glycosylation process of proteins in cells, glycosylation in most eukaryotes occurs commonly in the ER, i.e., yeast, insect, plant and mammalian cells share the features of N-linked oligosaccharide processing in the ER. Though the resultant glycoproteins in the ER have a near identical carbohydrate structure, with only the initial glycosylation in the ER, glycoproteins with a therapeutic efficacy cannot be fully produced.

The production of premature glycoprotein, which does not undergo the complete post-translational modification, may be caused by the deficiency of the terminal glycosylation machinery such as the Golgi apparatus. In other words, oligosaccharide processing by different cell types may diverge in the Golgi apparatus. The initial step in O-glycosylation by mammalian cells is the covalent attachment of N-acetylgalactosamine to serine or threonine. No O-glycosylation sequence has been identified analogous to the Asn-X-Ser/Thr template required for N-glycosylation. In further contrast to N-glycosylation, no preformed, lipid-coupled oligosaccharide precursor is involved in the initiation of mammalian O-glycosylation. Sugar nucleotides serve as the substrates for the first and all subsequent steps in O-linked processing. Following the covalent attachment of N-acetylgalactosamine to serine or threonine, several different processing pathways are possible for mammalian O-linked oligosaccharides in the Golgi. The oligosaccharide structures of glycoproteins can have a profound effect on properties critical to the human therapeutic use, including plasma clearance rate, antigenicity, immunogenicity, specific activity, solubility, resistance to thermal inactivation, and resistance to protease attack. Therefore, for a cell-free protein synthesis to be applied to the large-scale production of glycoprotein and for a rapid insight into the role of protein glycosylation to understand the relationship among stability, conformation, function of protein and glycosylation, an efficient cell-free completely post-translationally modified protein synthesis system in which protein is completely post-translationally modified needs to be developed.

For the production of proteins having the complete and correct structure, the present invention includes the combination of a cell-free protein synthesis system and co- and post-translational modification machinery containing organelles, separated from cells, relevant to co- and post-translational modification. This cell-free completely post-translationally modified protein synthesis method is a new approach that has not been attempted by anyone. This method is suitable especially to large-scale production of efficacious and useful proteins. Additionally, this method can be applied directly to post-translational modification processes, required to produce a biologically active protein besides glycosylation.

DETAILED DESCRIPTION OF THE INVENTION

Because of the inability of prokaryotes to modify proteins co- or post-translationally, the cell-free protein synthesis system used in the present invention must be derived from eukaryotes. Up to now, several sources of eukaryotic lysate (protein-synthesizing machinery) including fungi, mammalian cells (e.g., reticulocytes, endothelial cells, and lymphocytes), immortalized cell lines (e.g., cancer cell lines, etc.), plant cells (such as wheat germ or embryo cells, etc.) were used. And an efficient eukaryotic coupled cell-free transcription and translation system was developed using bacteriophage RNA polymerase and rabbit reticulocyte lysate (RRL) (U.S. Pat. No. 5,324,637). The terms "coupled transcription/translation system" and "coupled cell-free protein synthesis system" define the process whereby transcription and translation steps are carried out in sequence in a cell-free system. The terms "uncoupled cell-free protein synthesis system" and "cell-free translation system" apply to the process where the transcribed mRNA is purified after the initial transcription step and then the purified mRNA is transferred to a separate reaction system in which protein synthesis takes place.

As mentioned above, since the addition of only the ER cannot produce the completely post-translationally modified proteins, the addition of co- and post-translational modification machinery involved in terminal glycosylation is necessary. The addition of co- and post-translational modification machinery containing signal recognition particle, ER, Golgi apparatus, plasma membrane, and the like to the cell-free protein synthesis reaction mixture stimulates the production of completely post-translationally modified protein. A complete incubation mixture (containing the components of cell-free protein synthesis and co- and post-translational modification machinery) gives the completely post-translationally modified proteins. The events of the co- and post-translational modification process could be faithfully reproduced in vitro. The results described in the present invention have opened the possibility of a cell-free protein synthesis as an alternative to the in vivo production of pharmacological proteins and increased the understanding of the co- and post-translational modification process.

Cell sources for the preparation of the extract or lysate for the cell-free protein synthesis system and those for the co- and post-translational modification machinery may be the same or different. In the case of using the same cell, the extract or lysate for the cell-free protein synthesis system and the co- and post-translational modification machinery may be prepared separately or together.

The co- and post-translational modification machinery may be prepared from tissues and cultured cell lines. In glycosylation it is favorable to genetically engineer a cell source for the enhancement of the expression level of glycosylation related enzymes and/or for the enrichment of the pool of sugar nucleotides which serve as sugar donors in glycosylation. This type of genetic manipulation can be carried out by those skilled in the art; therefore, the detailed explanation is omitted in this specification.

As an example for obtaining the cell extract in the cell-free protein synthesis method, the preparation of nuclease-treated RRL and a crude homogenate from Chinese hamster ovary (CHO) cells are described in detail in Example 1 and 2, respectively. And the preparations of ER containing signal recognition particle, Golgi apparatus, and plasma membrane from a crude homogenate are described in detail in Example 3, 4, and 5, respectively.

In case of need, the glycoprotein produced by the cell-free protein synthesis method according to the present invention may be further modified through carbohydrate-adding reaction and/or carbohydrate-deleting reaction and/or carbohydrate-substituting reaction with enzymes relevant to the modification of side chains, e.g., glycosyltransferase, glycosidase, transglycosidase and so on. That means the addition, deletion, or substitution of carbohydrate side chains is possible. Furthermore, it is possible to introduce carbohydrate side chains not known in the general glycoprotein structures or to synthesize novel glycoprotein structures artificially, and thus the development of new glycoprotein is anticipated. For example, in the carbohydrate-adding reaction resultant itself or the erythropoietin (EPO) separated from it, sialic acid is further attached to the terminal chain thereof by transglycosidase which is one of carbohydrate chain addition enzymes, and the efficacy of glycoprotein increases with the addition of sialic acid to the terminal chain thereof.

The present invention can be applied to the production of proteins of therapeutic, commercial or research value. This includes proteins such as growth hormones, granulocyte colony stimulating factor, interleukin, interferon, thrombopoietin, tissue plasminogen activator and humanized monoclonal antibody. Additionally, the present invention not only produces the completely post-translationally modified protein but also can be used as a research tool in the form of a co- and post-translational modification kit in order to discover the function of a gene.

In one embodiment of the present invention, EPO was produced by cell-free completely post-translationally modified protein synthesis. However, it will be understood that the present invention is not limited to these specific examples, but is susceptible to various modifications that will be recognized by the skilled person in the present invention. Only an example of EPO glycosylation is disclosed but it is representative of all the different co- and post-translational modification. Therefore, the present invention includes all kinds of co- and post-translational modification.

EPO is a therapeutic glycoprotein currently used to treat anemia associated with several causes including chronic renal failure. EPO is a prime regulator of red blood cell production in mammals and birds. Specifically, this glycoprotein hormone promotes the rapid growth of red blood cell progenitors in marrow, spleen, and fetal liver, and subsequently is required for their terminal differentiation to circulating erythrocytes. Current therapeutic EPO is produced by animal cell culture.

The production of EPO via coupled cell-free completely post-translationally modified protein synthesis is described in detail in Example 6. And the production of EPO via uncoupled cell-free completely post-translationally modified protein synthesis is described in detail in Example 7. The production of EPO via combination of cell-free completely post-translationally modified protein synthesis and enzymatic in vitro glycosylation is described in detail in Example 8.

The present invention will now be illustrated by the following examples. The following examples serve to illustrate certain preferred embodiments and aspects of the present invention and are not to be construed as limiting the scope thereof.

EXAMPLE 1

The Preparation of Nuclease-Treated Rabbit Reticulocyte Lysate

Each animal was injected into the scruff of the neck with 4–5 ml of 1.25% (w/v) acetylphenylhydrazine (APH) solution each day on day 1, 2, and 3 of the schedule. An APH stock solution of 1.25% (w/v) in water was prepared on a heater-stirrer and stored at −20° C. The rabbits were normally bled on day 8 of the schedule. 0.5 ml of Hypnorm was injected into the thigh muscle. Once the Hypnorm had taken effect, and the rabbit rather dopey, the margin of one of the ears was shaved to expose the big marginal vein, which was injected with 2–2.5 ml of Nembutal or Sagatal containing 2000 units of heparin. When the animal was completely unconscious, the rabbit's chest was damped with 95% (v/v) ethanol, and the skin was cut away with a pair of sharp scissors. When the ribcage was well exposed, an incision from the bottom midline was made away, and up the midline toward the head, thereby making a triangular flap of flesh and bone with about 1-inch sides. The flap was folded open, and either the heart itself or one of the great vessels leading from the heart was cut. The chest cavity should rapidly be filled with blood, which was removed with a 30–50 ml syringe attached to a 3-inch long piece of silicone rubber or Tygon tubing into a chilled beaker in an ice bucket. An average of about 100 ml of blood was obtained from each rabbit.

The blood was filtered through cheesecloth or nylon mesh to remove hairs and debris. The cells were harvested from the blood by centrifugation with 500 ml polycarbonate bottles at 2,000 rpm for 10 min. After removal of the supernatant by aspiration, the cells were resuspended in buffered saline (5.5 mM KOAc, 25 mM Tris/acetate, 137 mM NaCl, 0.28 mM $Na_2HPO_4 \cdot 12H_2O$, 1 mM ethylenediaminetetraacetic acid (EDTA), and 1 mM dithiothreitol (DTF)) containing 5 mM glucose and spun again as before. The cells were washed additional three times, i.e., four low-speed spins altogether; on the last wash the volume of cells was determined by resuspending them in a measured volume of saline and measuring the total volume. After the final spin, as much of the saline as possible was removed and then 1.5 volumes (with respect to the packed cell volume) of ice-cold distilled water was added. The cells were mixed with the water thoroughly, and the contents of the different bottles were mixed with each other. The lysate was centrifuged for 20 min at 10,000 rpm (about 15,000 g) at 2° C. The supernatant was poured into a beaker through a fine nylon mesh (53 µm Nitex) to prevent any detached lumps of the glutinous stroma getting into the lysate; it contains inhibitor of protein synthesis.

For 400 µl of lysate, 8 µl of 1 mM hemin, 4 µl of 10 mg/ml creatine kinase solution, 3.2 µl of 125 mM $CaCl_2$ and 16 µl of 15,000 units/ml micrococcal nuclease solution were added and mixed thoroughly. The mixture was incubated for 30 min at 20° C. Digestion was stopped by adding 8.8 µl of 500 mM ethylene glycol-bis(2-aminoethyl ether)-N,N'-tetraacetic acid (EGTA); 4.8 µl of 10 mg/ml tRNA solution was added and mixed well. The lysate was dispensed in suitable aliquots of about 85 µl. The lysate was frozen in liquid nitrogen to achieve as rapid cooling as possible. Lysates stored in this way lost no activity over at least 3 years. Storage in a −70° C. freezer seemed to be satisfactory for periods of at least several months.

EXAMPLE 2

The Preparation of a Crude Homogenate from Chinese Hamster Ovary Cell

CHO cells were grown in two liters of cell culture media in 30 culture plates (15 cm diameter) at 34° C. for at least three generations (doubling time was approximately 20 h) to a density of about $5 \times 10^5$ cells/ml ($4-6 \times 10^7$ cells per plate). Cells were removed from the plates by trypsinization. The medium was aspirated, and each plate was rinsed with 10 ml of Tris-buffered saline (5.5 mM KOAc, 25 mM Tris/acetate, 137 mM NaCl, 0.28 mM $Na_2HPO_4 \cdot 12H_2O$, 1 mM EDTA, 1 mM DTT, and 0.5 mM phenylmethylsulfonyl fluoride (PMSF) (pH 7.4)). Then each plate was rinsed quickly with 5 ml of Tris-buffered saline containing 0.05% (w/v) trypsin and 0.02% (w/v) $Na_2EDTA$. After 5 min at room temperature, cells in each plate were suspended in 2 ml of ice-cold complete medium by pipetting and then pelleted by centrifugation for 5 min at 600 g at 4° C. The cell pellet was washed three times by repeated resuspension with 50–100 ml of Tris-buffered saline and centrifugation, and the packed cell volume was noted. The cell pellet was resuspended in homogenate buffer (250 mM sucrose, 10 mM Tris/acetate, 1 mM EDTA, 1 mM DTT, and 0.5 mM PMSF (pH 7.4)) to achieve a final volume equal to five times the volume of the cell pellet. A crude homogenate was made from this suspension of cells by stroking a very tight-fitting 15 ml Dounce homogenizer (Wheaton Co., Milliville, N.J.) 30 times. The crude homogenate obtained could be used at once or, more conveniently, frozen in liquid $N_2$ and stored at −80° C. for later subcellular fractionation.

EXAMPLE 3

The Preparation of Endoplasmic Reticulum Containing Signal Recognition Particle from a Crude Homogenate Frozen homogenate was thawed rapidly at 30° C. immediately before subcellular fractionation and thereafter maintained in ice. This crude homogenate was centrifuged for 15 min at 5,000 g at 4° C. The supernatant from the first differential centrifugation was further fractionated to yield ER fraction. The supernatant containing ER membranes was gathered, diluted with 4 volume of homogenate buffer, and centrifuged for 5 min at 8,500 g at 4° C. to remove contaminating mitochondria. The supernatant was top-loaded onto a discontinuous sucrose gradient consisting of 2.0 M sucrose-10 mM Tris/acetate (pH 7.4), 1.5 M sucrose-10 mM Tris/acetate (pH 7.4), and 1.3 M sucrose-10 mM Tris/acetate (pH 7.4) in a v/v ratio of 3:4:4. This gradient was centrifuged for 150 min at 90,000 g at 4° C. (Beckman SW28 rotor at 23,000 rpm) and ER fractions were collected at the 1.3 M-1.5 M interface and the 1.5 M-2.0 M interface. Gradient layers were diluted with 3 volume of dilution buffer (55 mM Tris/acetate and 5 mM $Mg(OAc)_2$ (pH 7.0)) and centrifuged for 45 min at 90,000 g at 4° C. The sedimented pellet was solubilized with storage buffer (50 mM Triethanolamine, 2 mM DTT, and 250 mM Sucrose).

ER can be treated with staphylococcal nuclease (EC 3.1.31.1) to deplete it of endogenous mRNA activity. To 0.1 ml fraction of ER, 8 µl of 12.5 mM $CaCl_2$ solution was added. Staphylococcal nuclease was added to a final concentration of 600 units/ml. Digestion was carried out for 30 min at 20° C. and quenched by the addition of 2.2 µl of 0.5 M EGTA solution (adjusted to pH 7.5 with NaOH). This nuclease-treated ER was frozen in liquid $N_2$ in 50 µl aliquots and stored at −80° C. Prior to use, frozen ER was thawed rapidly by brief exposure to 30° C. and then maintained in ice.

EXAMPLE 4

The Preparation of Golgi Apparatus from a Crude Homogenate

The frozen crude homogenate obtained was thawed rapidly at 30° C. immediately before subcellular fractionation and thereafter maintained in ice. This crude homogenate was centrifuged for 15 min at 5,000 g at 4° C. After an initial centrifugation at 5,000 g, most of the supernatant was removed and the yellow-brown portion (upper one-third) of the pellet was resuspended in a small amount of supernatant. After mixing, the sucrose concentration of 6 ml portions of the crude homogenate was adjusted to 1.4 M by adding 6 ml of ice-cold 2.3 M sucrose containing 10 mM Tris/acetate (pH 7.4). The $Na_2EDTA$ concentration was adjusted to 1 mM by adding 100 mM stock solution. The mixture was vortexed vigorously to ensure uniform mixing, loaded into an SW 28 tube (Beckman), and overlaid with 14 ml of 1.2 M sucrose-10 mM Tris/acetate (pH 7.4) and then 8 ml of 0.8 M sucrose-10 mM Tris/acetate (pH 7.4). This gradient was ultracentrifuged for 150 min at 90,000 g at 4° C. (Beckman SW28 rotor at 23,000 rpm). The turbid band at the 0.8 M-1.2 M sucrose interface was harvested in a minimum volume ($\leq$1.5 ml) by syringe puncture. Gradient layers were diluted with 3 volumes of dilution buffer (55 mM Tris/acetate and 5 mM $Mg(OAc)_2$ (pH 7.0)) and centrifuged for 45 min at 90,000 g at 4° C. The sedimented pellet was solubilized with storage buffer (50 mM Triethanolamine, 2 mM DTT, and 250 mM Sucrose). The fraction was immediately used or, more conveniently, frozen in liquid $N_2$ in suitable aliquots and stored at −80° C. The frozen Golgi apparatus fractions should only be thawed shortly before the assay by a minimal exposure to 30° C., and maintained in ice prior to use.

EXAMPLE 5

The Preparation of Plasma Membrane from a Crude Homogenate

The crude homogenate was centrifuged for 30 min at 25,000 g at 4° C. to prepare membrane-enriched microsome fraction. The supernatant was discarded and the pellets were resuspended in 0.2 M potassium phosphate buffer (pH 7.2) in a ratio of approximately 1 ml per pellet from $5\times10^8$ cells. The resuspended membranes then were loaded onto the two-phase system with a polymer mixture containing 6.6% Dextran T500 (Pharmacia Biotech), 6.6% (w/w) poly (ethylene glycol) 3350 (Fisher Scientific) and 0.2 M potassium phosphate (pH 7.2). The tubes were inverted vigorously for 40 times in the cold (4° C.). The phases were separated by centrifugation at 1,150 g for 5 min at 4° C. The upper phase containing primarily plasma membranes was diluted with 1 mM bicarbonate and collected by centrifugation at 30,000 g for 15 min.

EXAMPLE 6

The Production of EPO via Coupled Cell-Free Completely Post-Translationally Modified Protein Synthesis The plasmid, p64T-EPO containing the cDNA of human EPO with its authentic signal sequence (Boissel, J. P., et al., J. Biol. Chem. 268:15983–15993 (1993)) was purified with cesium chloride gradient ultracentrifugation and used as the template for coupled cell-free completely post-translationally modified protein synthesis. The cell-free completely post-translationally modified protein synthesis was carried out in the presence of the co- and post-translational modification machinery including glycosylation machinery besides the components of cell-free protein synthesis. The reaction mixture contained about 53% (v/v) nuclease-treated RRL and the final concentrations of other key components were: 17 mM creatine phosphate, 48 μg/ml creatine phosphokinase, 40 μM each amino acid, 260 units/ml SP6 RNA polymerase, 75 μg/ml circular plasmid DNA, 1.8 mM ATP, 1.3 mM GTP, 1 mM each of UTP and CTP, 50 mM potassium acetate, 3.6 mM magnesium acetate, 0.4 mM spermidine, 4 mM Hepes/KOH (pH 7.3), 1600 units/ml ribonuclease inhibitor, 2.7 mM DTT, 9.5 μM hemin, and 57 μg/ml calf liver total tRNA mixture. The reaction mixture was incubated for 60 min at 30° C.

Figure 1:
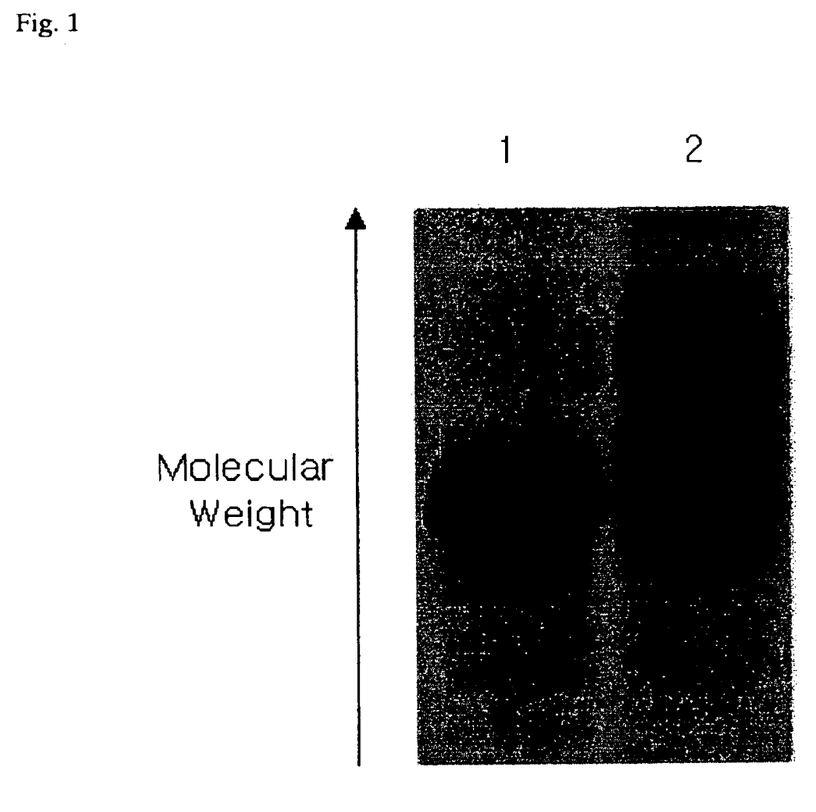
FIG. 1 shows an autoradiogram of completely post-translationally modified EPO by the method disclosed in the present invention and unmodified EPO that have been separated by SDS-polyacrylamide gel electrophoresis.

FIG. 1 shows an autoradiogram of completely post-translationally modified EPO by the method disclosed in the present invention and unmodified EPO that has been separated by SDS-polyacrylamide gel electrophoresis. Lane 1 shows EPO produced by cell-free protein synthesis without co- and post-translational modification machinery, Lane 2 shows EPO produced by cell-free completely post-translationally modified protein synthesis. In Lane 2, the increase in molecular weight of the EPO molecule implies that EPO has been glycosylated.

Figure 2:
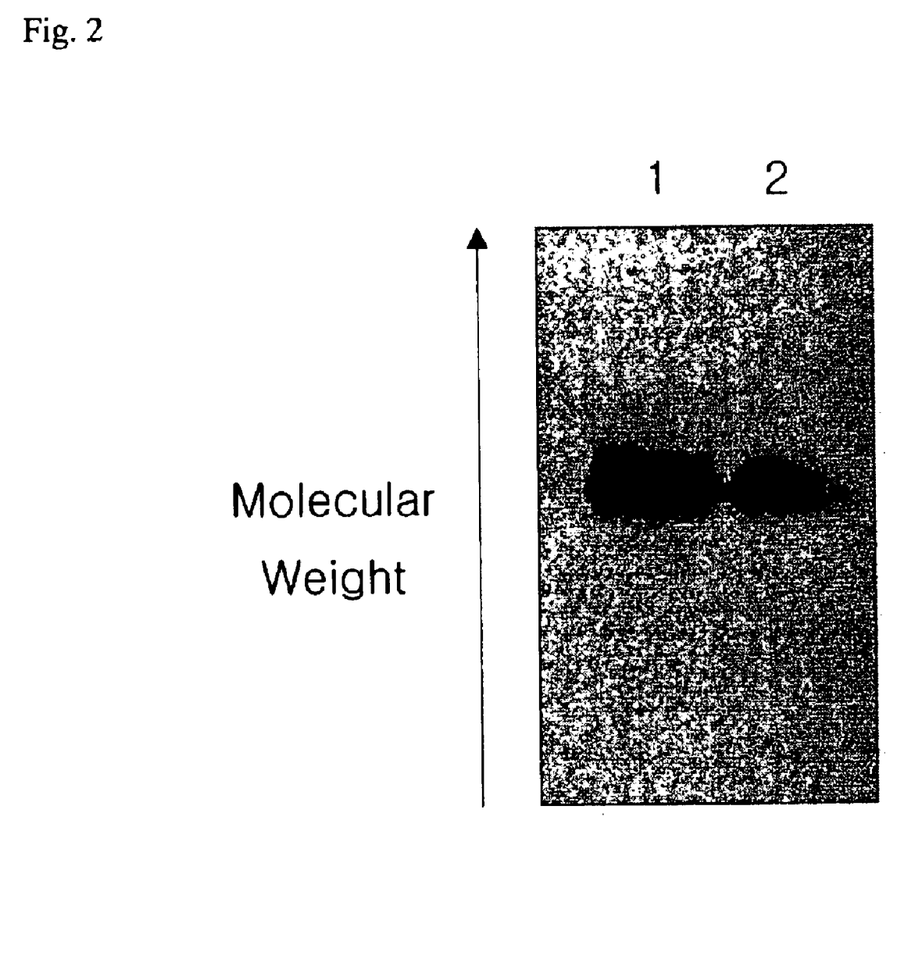
FIG. 2 shows the result of western blotting of EPO produced by a conventional cell culture method and by the present invention.

FIG. 2 shows the result of western blotting of EPO produced by a conventional cell culture method and EPO produced by a cell-free completely post-translationally modified protein synthesis of the present invention. Lane 1 shows EPO produced by a conventional cell culture method, Lane 2 shows EPO produced by a cell-free completely post-translationally modified protein synthesis. As shown by Lane 2, EPO produced by the present invention has the same molecular weight as EPO produced by conventional cell culture method and has the characteristic reactivity towards EPO specific antibody.

Figure 3:
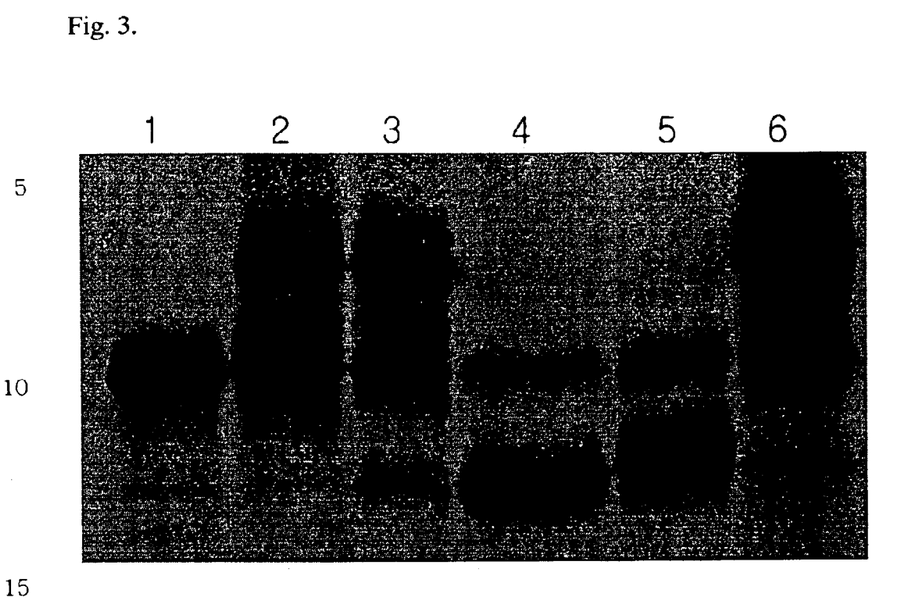
FIG. 3 shows an autoradiogram of EPO treated with glycosidase.

FIG. 3 shows an autoradiogram of EPO treated with glycosidase. Glycosidase selectively cleaves the carbohydrate chain from the protein. Lane 1 shows nonglycosylated EPO, Lane 2 and 3 shows glycosylated EPO, Lane 4 and 5 shows EPO treated with glycosidase F, and Lane 6 shows EPO treated with glycosidase H. It is reported that biologically active EPO possesses complex type oligosaccharide. This complex type oligosaccharide is known to be cleaved by glycosidase F and not by glycosidase H. As FIG. 3 shows, EPO produced by cell-free completely post-translationally modified protein synthesis is resistant to glycosidase H and cleaved by glycosidase F and thus contain the correct and complete complex-type oligosaccharide structure.

As the results of FIGS. 2 and 3 show, it can be concluded that EPO produced by cell-free completely post-translationally modified protein synthesis of the present invention contains the same structure as EPO produced by conventional cell culture methods.

For the solubilization of membrane, the reaction mixture was treated with 0.5% Triton X-100. And then the synthesized EPO was immuno-purified with monoclonal antibody to EPO using general procedure.

After dialysis in refolding solution (50 mM sodium dihydrogenphosphate, 2%(v/v) sodium lauryl sarcosylate, 40 μM cupric sulfate), EPO was lyophilized. Purified EPO was subjected to biological activity test described as follow.

The biological activities of the purified EPO in vitro and in vivo were assayed by the growth of the EPO-dependent human cell-line, TF-1, cultured in RPMI 1640 medium containing 10% fetal calf serum (Kitamura, T. et al., Blood 73:375–380 (1989)) and by the incorporation of $^{59}Fe$ into erythroblast cells of exhypoxic polycythemic mice (Goldwasser, E. and Gross, M., Methods in Enzymol. 37:109–121 (1975)), respectively. Values were determined by a parallel line assay (Dunn, C. D. R. and Napier, J. A. P., Exp. Hematol. (N.Y.) 6:577–584 (1978)) using nine doses/sample and two wells/dose for the in vitro assay, and more than three doses/sample and three mice/dose for the in vivo assay. Any additives in the EPO preparations, such as salts, did not interfere with the assay when used at 1/500 dilution with the medium. The highly purified recombinant human EPO (rHuEPO) calibrated by the second International Reference Preparation was used as standard. As predicted, the results conclude that the purified EPO showed similar in vitro and in vivo activities compared with the intact rHuEPO.

EXAMPLE 7

The Production of EPO via Uncoupled Cell-Free Completely Post-Translationally Modified Protein Synthesis The plasmid, p64T-EPO containing the cDNA of human EPO with its authentic signal sequence was purified with cesium chloride gradient ultracentrifugation and used as the template for in vitro transcription. In vitro transcription was carried out with or without cap structure, $^7mG(5')ppp(5')G$. The final optimized concentrations of components for in vitro transcription without cap structure were: 40 mM Tris-HCl (pH 7.5), 6 mM magnesium chloride, 10 mM DTT, 1 mM each NTP, 1000 units/ml ribonuclease inhibitor, 2 mM spermidine, 1000 units/ml SP6 RNA polymerase, 10 mM sodium chloride and 0.1 mg/ml circular plasmid. The final optimized concentrations of components for in vitro transcription with cap structure were: 40 mM Tris-HCl (pH 7.5), 6 mM magnesium chloride, 10 mM DTT, 1 mM each ATP, CTP and UTP, 0.5 mM GTP, 1000 units/ml ribonuclease inhibitor, 2 mM spermidine, 1000 units/ml SP6 RNA polymerase, 10 mM sodium chloride, 0.5 mM cap analog and 0.1 mg/ml circular plasmid. To avoid precipitation of DNA with spermidine, the reaction mixture was pre-warmed at 37° C. prior to the addition of DNA. The transcription reaction was carried out at 37° C. for 4 h. For the isolation of synthesized RNA, the reaction mixture was extracted with phenol/chloroform and then with chloroform alone. RNA was selectively precipitated by addition of equal volume of 5 M LiCl and incubation in ice for 1 h. Then the mixture was centrifuged for 15 min at 5,000 g at 4° C. The resulting pellet was washed with 75% (v/v) ethanol and redissolved in RNase-free water. The uncoupled cell-free protein synthesis in the presence of the co- and post-translational modification machinery including glycosylation machinery was carried out. The reaction mixture contained about 53% (v/v) nuclease-treated RRL and the final concentrations of other key components were: 17 mM creatine phosphate, 48 µg/ml creatine phosphokinase, 40 µM each amino acid, 30 µg/ml RNA, 0.8 mM ATP, 0.3 mM GTP, 50 mM potassium acetate, 0.5 mM magnesium acetate, 0.4 mM spermidine, 4 mM Hepes/KOH (pH 7.3), 1600 units/ml ribonuclease inhibitor, 2.7 mM DTT, 9.5 µM hemin, and 57 µg/ml calf liver total tRNA mixture. The reaction mixture was incubated for 60 min at 30° C.

Figure 4:
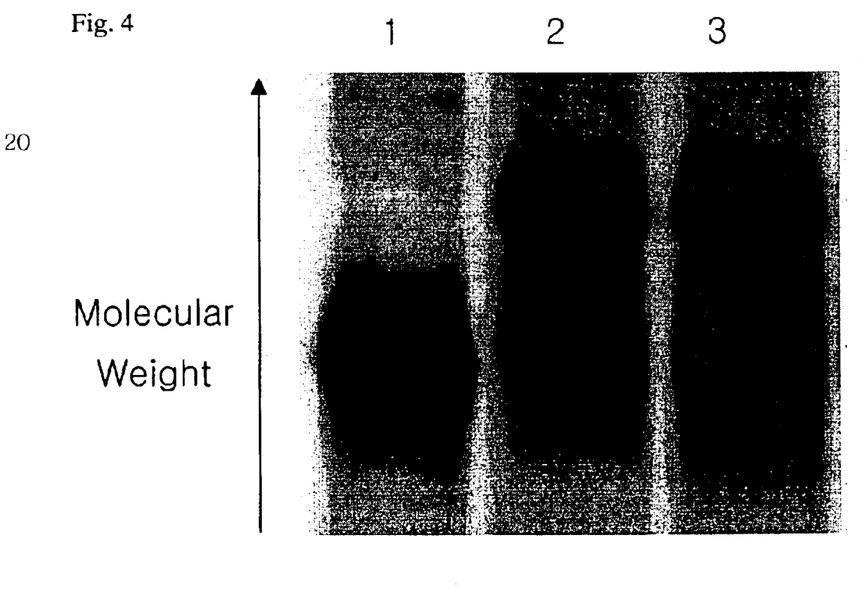
FIG. 4 shows an autoradiogram of EPO produced by an uncoupled cell-free completely post-translationally modified protein synthesis and by a coupled cell-free completely post-translationally modified protein synthesis.

EPO produced by this method is shown in FIG. 4 to be the same as the EPO produced in example 6. In FIG. 4, lane 1 shows EPO produced by cell-free protein synthesis without co- and post-translational modification machinery, lane 2 shows EPO produced by an uncoupled cell-free completely post-translationally modified protein synthesis and lane 3 shows EPO produced by a coupled cell-free completely post-translationally modified protein synthesis.

For the solubilization of membrane, the reaction mixture was treated with 0.5% Triton X-100. And then the synthesized EPO was immuno-purified with monoclonal antibody to EPO using general procedure. After dialysis in refolding solution (50 mM sodium dihydrogenphosphate, 2% (v/v) sodium lauryl sarcosylate, 40 µM cupric sulfate), EPO was lyophilized. Purified EPO was subjected to biological activity test described as example 6. As a result, the purified EPO showed similar in vitro and in vivo activities compared with the intact rHuEPO.

EXAMPLE 8

The Production of EPO via Combination of Cell-Free Completely Post-Translationally Modified Protein Synthesis and Enzymatic in vitro Glycosylation The EPO produced by either coupled or uncoupled completely post-translationally modified protein synthesis system described in Examples 6 and 7 may be further modified by enzymes such as glycosyltransferase, glycosidase, and transglycosidase.

After the cell-free completely post-translationally modified protein synthesis, the reaction mixture was treated with 0.5% Triton X-100 to solubilize the membrane. And the reaction mixture or affinity-purified EPO was treated with other modifying enzymes. This example describes the use of trans-sialidase. A crude preparation of trans-sialidase was obtained as described previously (Cavallesco, R. and Pereira, M. E. A., J. Immunol. 140:617–625 (1988); Prioli, R. P., et al., J. Immunol. 144:4384–4391 (1990)).

5 µl of 0.5 µg/ml trans-sialidase was added to 15 µl of cell-free completely post-translationally modified protein synthesis reaction mixture containing 0.25 µmol of 2,3-sialyllactose or p-nitrophenyl-α-N-acetylneuraminic acid. In case of affinity-purified EPO, 10 µl of 0.5 µg/ml trans-sialidase was added to 40 µL of 50 mM cacodylate/HCl buffer (pH 6.9) containing 0.25 µmol of 2,3-sialyllactose or p-nitrophenyl-α-N-acetylneuraminic acid. After incubation at 30° C. for 18 h, the sialylated EPO was purified by affinity chromatography as aforementioned procedure in example 6 and subjected to methylation analysis. The sialylated product was converted to the corresponding permethylated monosaccharide alditol acetate as previously described (Scudder, P., et al., Eur. J. Biochem. 168: 585–593 (1987)). The derivatized samples were analyzed on a Hewlett-Packard 5890A capillary gas chromatography equipped with a 0.25 mm×30-m fused silica DB5 capillary column (J & W Scientific) which, after a 5-min hold time, was ramped from 150 to 230° C. at a rate of 2° C./min. The EPO treated with trans-sialidase featured a 10% elevation in sialic acid content and a 15% enhancement in biological activity. On average sialic acid increased from 11.9 mol to 13 mol per mol of EPO.

From the above, it should be evident that the present invention provides an efficient and consistent cell-free completely post-translationally modified protein synthesis system. It should be understood that the present invention is not limited to the specific compositions or methods shown nor to the particular uses of the compositions described. In light of the foregoing disclosure, it will be apparent to those skilled in the art that substitutions, alterations, and modifications are possible in the practice of this invention without departing from the spirit or scope thereof.

Equivalents

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A method for in vitro syntheses, translocation, post-translational modification and secretion processing of a protein comprising:
   a. adding DNA or RNA encoding said protein to a reticulocytes lysate translation system,
   b. adding a post-translational modification machinery comprising endoplasmic reticulum, Golgi apparatus and plasma membrane obtained from a Chinese Hamster Ovary (CHO) cell to said translation system to produce a reaction mixture,
   c. incubating the reaction mixture to yield a protein-containing reaction mixture containing a translated and modified protein, and
   d. purifying translated and modified protein.

2. The method according to claim 1, wherein the protein is erythropoietin.

3. The method according to claim 1, wherein the post-translational modification machinery is prepared from a genetically modified Chinese Hamster Overy (CHO) cell which is modified to have enriched levels of sugar neclevotides.

4. The method according to claim 1, wherein the protein is further modified through carbohydrate-modifying reaction with enzymes relevant to the modification of a glycosylated side chain.

5. The method according to claim 1, wherein the post-translational modification machinery is prepared from a genetically modified Chinese Hamster Overy (CHO) cell which is modified to have enhanced levels of glycosylation enzymes.

6. The method according to claim 1, wherein the protein is selected from the group consisting of erythropoietin, growth hormones, granulocyte colony stimulating factor, interleukin, interferon, thrombopoietin, tissue plasminogen activator, and humanized monoclonal antibody.

7. The method according to claim 3, wherein the protein is selected from the group consisting of erythropoietin, growth hormones, granulocyte colony stimulating factor, interleukin, interferon, thrombopoietin, tissue plasminogen activator, and humanized monoclonal antibody.

8. The method according to claim 4, wherein the protein is selected from the group consisting of erythropoietin, growth hormones, granulocyte colony stimulating factor, interleukin, interferon, thrombopoietin, tissue plasminogen activator, and humanized monoclonal antibody.

9. The method according to claim 5, wherein the protein is erythropoietin.

* * * * *